United States Patent [19]

Baker, Jr. et al.

[11] 4,280,502

[45] Jul. 28, 1981

[54] TACHYCARDIA ARRESTER

[75] Inventors: Ross G. Baker, Jr., Lake Jackson; Richard Van Calfee, Houston, both of Tex.

[73] Assignee: Intermedics, Inc., Freeport, Tex.

[21] Appl. No.: 64,553

[22] Filed: Aug. 8, 1979

[51] Int. Cl.³ ............................................. A61N 1/36
[52] U.S. Cl. ............................................. 128/419 PG
[58] Field of Search ..................... 128/419 D, 419 PG

[56] References Cited

U.S. PATENT DOCUMENTS

| | | | |
|---|---|---|---|
| 3,693,627 | 9/1972 | Berkovits | 128/419 PG |
| 3,921,642 | 11/1975 | Preston et al. | 128/419 PG |
| 3,939,844 | 2/1976 | Pequignot | 128/419 PG |
| 3,942,534 | 3/1976 | Allen et al. | 128/419 PG |

*Primary Examiner*—William E. Kamm

*Attorney, Agent, or Firm*—Bard & Groves

[57] ABSTRACT

A method and apparatus are provided for detecting and arresting a condition of tachycardia. Stimulating pulses are provided in a search routine within a selected time interval after a tachycardia beat. The heart is monitored after each pulse application and the search is terminated when a normal heartbeat is detected. In a preferred search routine, the refractory interval of the heart adjacent the electrode is determined during a first search routine. If the first search routine does not terminate the tachycardia, the refractory interval found during the search is stored. A second pulse is then applied in a time interval following the refractory interval pulse to break the tachycardia. The breaking interval is determined through a second search routine generated in an interval following the refractory interval pulse.

35 Claims, 7 Drawing Figures

TACHYCARDIA ARRESTER

FIELD OF THE INVENTION

This invention relates to implanted cardiac stimulators, and more particularly, to implanated cardiac stimulators which detect the occurrence of tachycardia and derive one or more stimulating pulses in a temporal relationship to naturally occurring cardiac stimulus to arrest the tachycardia.

BACKGROUND OF THE INVENTION

There are many arrhythmias which can occur to affect the ability of the heart to effectively pump blood. In a normal heart, a stimulating pulse originates at the sinus node and is conducted throughout the heart by various conductive bundles causing sequential atrial and ventricular contractions to pump blood through the heart. One form of arrhythmia involves a complete blockage of the normal conductive paths whereby the exciting pulse is blocked from reaching a portion of the heart to cause a contraction. Implanted cardiac pacers have long been available to detect such a heart blockage and provide a substitute stimulating pulse at a location which avoids the blockage.

Yet another arrhythmia with serious consequences is tachycardia, a condition where an abnormally high heart beat rate occurs. Tachycardia severly affects the ability of the heart to pump blood and the higher the heart beat rate, the more dangerous the condition.

There are many mechanisms which have been postulated as the cause of a tachycardia. A first mechanism is abnormal automaticity which involves a basic malfunction of heart tissue. The present invention does not concern this basic malfunction.

A second cause of tachycardia involves a rapidly circulating impulse in a circus pathway. This condition is typically called reentry tachycardia. In general, a reentry path may be established when a normal pathway is blocked while alternate pathways remain conducting. If the conduction velocity of the pathway and the refractory period of the heart tissue obtain a critical relationship, a reentry tachycardia may be initiated.

During the refractory period, the heart muscle is insensitive and will not respond to an arriving signal. However, a response may be obtained as soon as the muscle has recovered. Accordingly, if the signal completes its circus movement as the muscle concludes the refractory period, a reentry path is established and a condition of tachycardia now exists. Heartbeat rates of well over 200/minute are not uncommon.

It has been found that a tachycardia based upon reentry may be stopped by refractory tissue in the reentry pathway. Stimulating pulses may be introduced to the heart to create refractoriness ahead of the circulating impulse. As hereinbelow discussed, it is known that the arrival of a single stimulating pulse at a critical moment may terminate the tachycardia. Where a single pulse is not effective, two or more stimulating pulses may be introduced. A first pulse creates an area of tissue in a refractory period around the site of the stimulation. A second pulse applied at the stimulation site can then be applied at an interval effective to produce refractory tissue ahead of the circulating impulse.

PRIOR ART

Control of tachycardia has generally occurred in a clinical situation where the stimulating pulse generator is located externally of the patient so that stimulating pulse timing can be varied. Where a single pulse has been employed, the pulse frequency has been chosen either greater than or lesser than the naturally occurring tachycardia whereby the applied pulses occur randomly between tachycardia beats until a pulse happens to occur at the critical point to block the tachycardia. In some instances, an extremely high pulse rate may be effective to terminate the tachycardia. In either event, the timing of the pulse is random with respect to the tachycardia. In one laboratory procedure, an intra-atrial "P" wave provides the trigger for an impulse delivered at predetermined intervals after the "P" wave.

Where two stimulating pulses are applied, a fixed coupling interval has been employed. The coupled pulses are then applied at a rate slightly different than the tachycardia to affect a scan of the cardiac cycle until the coupled pulses occur at a time which happens to arrest the tachycardia. The fixed coupling interval may be varied during successive scan cycles until an effective coupling interval is found which terminates the tachycardia. Control of the coupling interval is manual and no provision was included for checking the efficacy of a given coupled stimulus after application of one pair of stimulating pulses. Indeed, the scanning approach requires that sufficient time elapse to complete the scan before it is known that the selected coupling interval is not effective.

A general discussion of the nature of the problem may be found in an article by H. J. J. Wellens "Value and Limitations of Programmed Electrical Stimulation of the Heart in the Study and Treatment of Tachycardias", 57 Circulation 845, 1978. More detailed discussion of clinical techniques are available in articles by J. I. Haft, "Treatment of Arrhythmias by Intra-Cardiac Eelectrical Stimulation", 16 Prog. in Cardiovasc. Dis. 539 (1974), and by R. A. J. Spurrell and E. Sowton, "The Management of Paroxysmal Supraventricular Tachycardia Using a Scanning Pacemaker System", and "Cardiac Pacing" 187-190, ed. Yoshio Watanabe (1977). The only implanted cardiac pacer discussed in these references is one having at least one fixed rate greater than the expected rate for the tachycardia. When the patient detects a tachycardia, a magnet activates a reed switch in the implanted unit whereby the higher fixed rate is selected to suppress the tachycardia. The unit paces until the activating magnet is removed from adjacent the reed switch.

As seen from the above discussion, the prior art does not actively seek a pair of pulses applied at times effective to terminate the tachycardia. A first pulse may be applied at an interval following a naturally occurring heartbeat but the interval is varied only in response to a prolonged continuation of the tachycardia. Further, the coupled pulse interval is fixed at least during a given scan, lengthening the time required to terminate the tachycardia.

The prior art treats each tachycardia as a new event. The arrest routine begins with the same initial trial pulse intervals for every occurrence without regard for past successes. These and other advantages of the prior art are overcome by the present invention which provides improved method and apparatus in a cardiac stimulator for arresting a tachycardia.

Accordingly, it is an object of the present invention to provide a cardiac pacer for the automatic detection and arrest of tachycardia.

Another object is to apply either a single or a double pulse, whichever has been previously determined effective to arrest the tachycardia.

Yet another object is to apply a pulse or pulses with reference to naturally occurring heartbeats.

One other object is to apply a first arresting pulse at the end of a refractory period which has been determined by sequential trial stimuli.

An object is to apply a second arresting pulse within a measured tachycardia interval.

Yet another object is to variably apply the second arresting pulse in a preselected sequence within the measured tachycardia interval until an arrest occurs.

One other object is to store successful arrest parameters as starting parameters for arresting a subsequent tachycardia.

SUMMARY OF THE INVENTION

Method and apparatus for detecting and arresting a tachycardia are provided. Stimulating pulses are provided in a predetermined temporal relationship with naturally occurring heart beats to affect a search routine leading to termination of the tachycardia. After the application of each pulse, the heart is monitored for termination of the tachycardia.

In a preferred search routine, the refractory interval of the heart adjacent the electrode is determined from a first search routine. If the first search routine does not result in termination of the tachycardia, the refractory interval found during the search is stored. A second pulse is then applied following the found refractory interval pulse by a breaking interval. The breaking interval is determined by a second pulse and search routine during a tachycardiac interval following the refractory interval pulse.

Refractory and breaking intervals determined to be successful for terminating a tachycardia are stored for later initial application during a subsequent tachycardia. If desired, a single pulse application mode may be selected where only a breaking interval is determined for tachycardia arrest.

It is a feature of the present invention to detect the occurrence of a tachycardia and automatically initiate a trial search for a pulse effective to terminate the tachycardia.

It is another feature that the trial search interval for pulse application is initiated by natural heartbeats.

Yet another feature of the present invention is that a preselected pattern of varying trial search intervals is used to obtain a pulse at an interval effective to terminate the tachycardia.

IN THE DRAWINGS

DETAILED DESCRIPTION OF THE DRAWINGS

Figure 1:
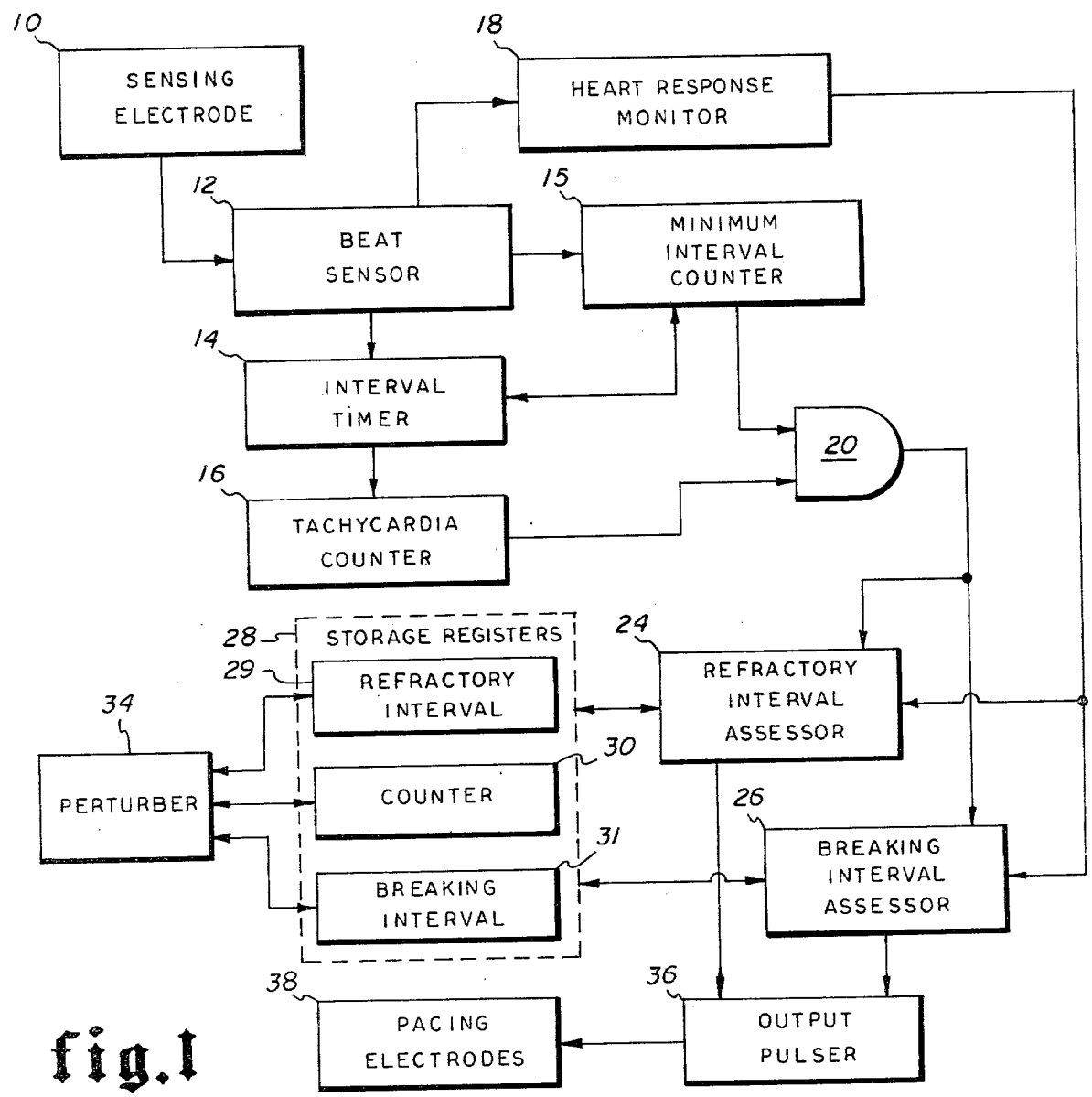
FIG. 1 is a block diagram functionally representing a tachycardia arrest system.

Referring now to FIG. 1, there may be seen a functional block diagram for the tachycardia arrest system. As hereinbelow described, it is intended that the tachycardia arrest system be fully implantable in cooperation with a conventional cardiac pacer. The system may, however, be conveniently used in a clinical situation, where it is desired to monitor the patient's response prior to implanting any cardiac pacer.

Sensing electrode 10 and pacing electrode 38 are placed adjacent the desired portion of the heart which is to be stimulated. The pacing electrode may be placed in the atrium, where the sinus node is located, since the atrium is a common source of reentry tachycardia. In some instances, however, pacing electrode 38 may be inserted into the ventricle or a plurality of pacing electrodes 38 may be provided adjacent both the atrial and ventricular tissue.

Sensing electrode 10 is placed in a region proximal to the pacing electrode 38 and detects tissue response to the stimulating pulse. A plurality of sensing electrodes 10 may be provided in correspondence with a plurality of pacing electrodes 38. In general, a sensing electrode 10 located in the atrium will be interconnected to respond to the "P" wave originating from the sinus node. A sensing electrode 10 located in the ventricle will be set to respond to the "QRS" wave originated from the A-V node.

A wide variety of suitable electrodes are conventionally available, including bipolar electrodes and quadpolar electrodes. Thus, the proper electrode configuration may be selected to provide for stimulating the desired portions of the heart.

As may be seen in FIG. 1, the output from sensing electrode 10 is provided to beat sensor 12 for generating a suitable electrical signal corresponding to the occurrence of a naturally occurring signal wave. Beat sensor 12 may conveniently provide an output of heart response monitor 18 and to timers 14 and 15. Minimum interval timer 15 is set to an interval selected to correspond with a known ineffective stimulating interval. That is, a constant interval within which a stimulating pulse will always be ineffective.

Interval timer 14 receives an input from beat sensor 12 and minimum interval timer 15 to provide an output to tachycardia counter 16. Thus, when the interval between successive heart beats is less than a preselected interval, interval timer 14 provides an output to tachycardia counter 16. In a preferred embodiment of the present invention, the occurrence of a predetermined number of such tachycardiac intervals must occur in succession in order to enable the system to initiate an output to arrest the tachycardia. In one embodiment, a heart beat rate of greater than 150/minutes is selected to represent a tachycardia. The corresponding interval is 400 msec. The occurrence of five successive heart beats having an interval of 400 msec or less is selected to indicate the condition of tachycardia.

It will be appreciated that any number of suitable combinations of heart beat rates and occurrence requirements may be selected to initiate system operation.

Once the selected number of successive outputs have been received which indicate tachycardia, tachycardia counter 16 provides an output to AND gate 20. Minimum interval timer 15 also provides an output to AND gate 20 when the minimum interval is exceeded for each succeeding output from beat sensor 12. Thus, an enabling output is provided from AND gate 20 whenever a tachycardia has been detected and whenever the heart is near a condition responsive to arrest the tachycardia.

The tachycardia arrest system depicted in FIG. 1 has two pulse generating systems. A first pulse generating system, refractory interval accessor 24, provides a stimulating pulse as adjacent heart tissue is just recovering from the refractory period introduced by the circulating natural signal. A second signal generating system, breaking interval assessor 26, provides a stimulating pulse in the interval between the refractory interval and the tachycardia interval at a time which is found to be effective to arrest the tachycardia in the manner hereinafter described. Breaking interval assessor 26 may be selected to provide a single arresting pulse or may cooperate with refractory interval assessor 24 to provide variable temporally spaced pulses for breaking the tachycardia.

A storage register unit 28 is provided for storing various parameters which are tried during a refractory interval assessment and a breaking interval assessment, and also for storing successful parameters. Thus, refractory interval storage register 29 and breaking interval storage register 31 are provided. Counter 30 may be provided, as hereinbelow explained, for controlling the selection of temporal relationship between the tachycardia signals and the generated signals.

In a preferred embodiment of the tachycardia arrest system, when the tachycardia has been arrested, the successful parameters are stored in refractory interval register 29 and breaking interval register 31. When a subsequent condition of tachycardia occurs, the previously successful parameters are recalled from storage register 28 and the tachycardia arrest system first tries those successful parameters to arrest the tachycardia. If the stored parameters are not again successful, perturber 34 provides for slight alterations of the successful parameters to arrest the tachycardia. Perturber 34 operates on the assumption that slight variations of the successful parameter within defined limits may act to arrest the tachycardia without initiating the entire assessment search again. Clinical data indicates that perturbing the breaking interval plus or minus 8 msec about the previous successful interval will frequently yield success.

If a two pulse arrest technique has been selected, the refractory interval is first established. Frequently, the search for the refractory interval will break the tachycardia. As hereinbelow discussed, refractory interval assessor 24 initiates an output pulse from output pulser 36 which is conducted to pacing electrode 38 for application to the heart. The response of the heart is then sensed by sensing electrode 10 and detected by beat sensor 12 and heart response monitor 18 for feedback to refractory interval assessor 24. The output from refractory interval assessor 24 is applied at various times in the interval between the end of the minimum interval and the tachycardia signal until the refractory interval is established or until arrest of the tachycardia is detected.

Once the refractory interval is established, breaking interval assessor 26 operates to generate a second pulse in the interval between the end of the refractory period and the occurrence of the tachycardia signal. The refractory interval pulse is applied and then the breaking interval pulse is applied at a first selected time. The heart response is monitored to determine whether a condition of tachycardia still exists. If the next input from sensor electrode 10 is still within the tachycardia interval, breaking interval assessor 26 will generate the second stimulating pulse at a different spacing from the refractory interval pulse. The spacing variations will then be provided in a preselected manner until the tachycardia is arrested. The response of the heart to each pair of pulses is monitored and the system is disenabled as soon as a normal cardiac interval is restored and detected.

Figure 1A:
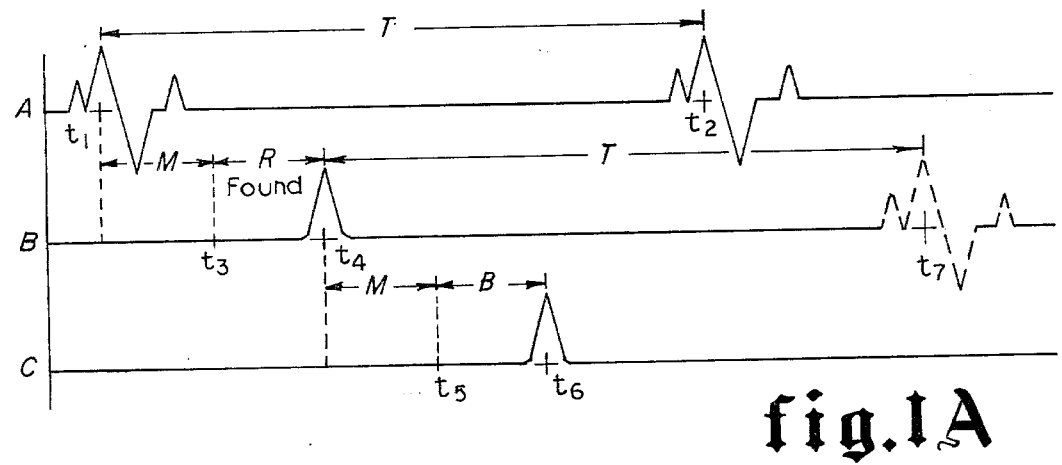
FIG. 1A is a timing chart of the various signals.

FIG. 1A illustrates the relative relationships of the various signals discussed above. Tachycardia hearts are shown on line A occurring at $t_1$ and $t_2$ with an interval T. The beat at $t_1$ initiates a refractory interval pulse.

A fixed minimum interval M is used to eliminate a portion of interval T where the heart tissue adjacent the electrode will be refractory. The refractory interval R is the interval found during the search where an applied pulse is effective to again stimulate the tissue. The next tachycardiac heart beat would be expected to occur at an interval T after $t_4$ at $t_7$.

The breaking interval is assessed in the interval T following $t_4$. Again, a minimum interval M is provided to eliminate a known refractory period. The breaking interval B between $t_5$ and $t_6$ is found by actively searching the interval between $t_5$ and $t_7$ until an effective breaking interval B is found, as hereinafter described.

Figure 2:
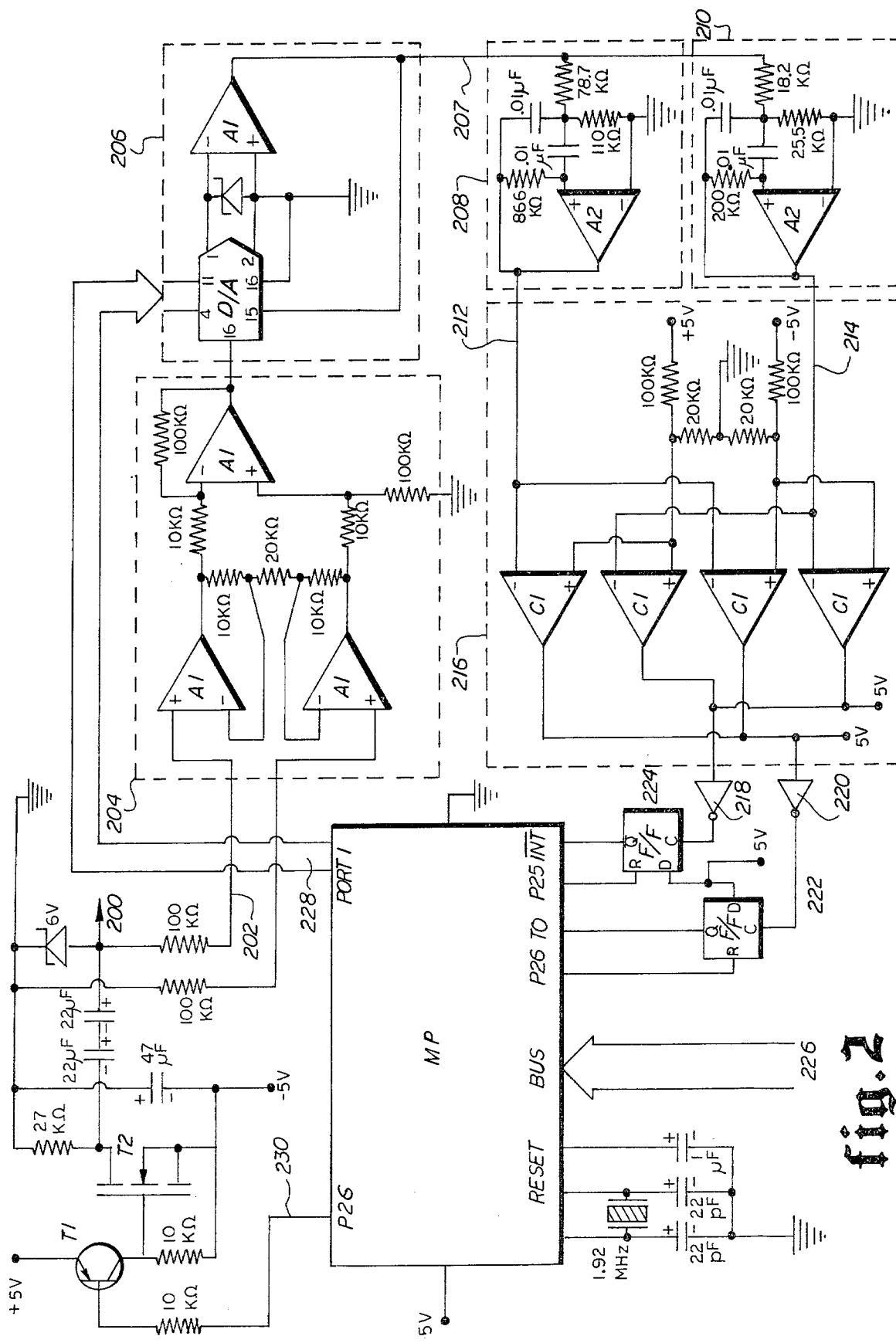
FIG. 2 is a circuit diagram of a tachycardia arrest system.

Referring now to FIG. 2, there may be seen a circuit schematic more particularly depicting a microprocessor controlled circuit for accomplishing the functions herein discussed in FIG. 1. Although discreet components could be utilized, the ready availability of sophisticated microprocessors and the size and reliability advantages obtained thereby, make microprocessors a preferred embodiment for a cardiac pacer-type application. A catheter electrode lead assembly 200 may provide both the input signal information and deliver output pulses to the heart, or separate leads could be employed if desired.

The input signal 202 from catheter 200 is first amplified by amplifier 204. A plurality of linear amplifiers A1 are provided in a conventional instrumentation amplifier arrangement to provide an output signal to variable gain control circuit 206.

Variable gain control circuit 206 incorporates a digital-to-analog D/A circuit which is controlled by a digital output 228 from MP, the microprocessor in the system.

Output signal 207 from gain control circuit 206 is then presented to low pass filter 208 and high pass filter 207. Low pass filter 208 and high pass filter 210 are conventional active filter elements employing linear amplifiers A2. Low pass filter 208 may typically have a band pass region of 10–40 Hz for processing the actual heartbeat signal. The high pass filter 210 presents an output 214 which is functionally related to the occurrence of noise, either within or without the patient.

Heartbeat frequency signal 212 and noise frequency signal 214 are next converted to pulse-type signals by absolute value comparator circuit 216. A pair of two comparator C1 absolute value circuits are formed, one each for heart signal 212 and noise signal 214. Thus, an input signal either above or below the reference signal will cause the output of the paired comparators to go low.

The outputs from absolute value comparator 216 are presented to inverters 220 and 218 to form positive pulse signals 222, functionally related to the heartbeat frequency, and 224, functionally related to noise, respectively.

The noise input signal 224 is presented to the clock input of a flip-flop F/F. The affect of the noise signal on system operation is not a subject of the present patent application but if a sufficient number of noise pulses are accumulated, the system reverts to a fixed rate pacing mode of operation in accordance with conventional teachings. A fixed rate mode is appropriate when the pacer circuitry can no longer reliably sense heart operation and must override naturally occurring heartbeats, if any, until the source of the noise is removed.

The heartbeat frequency signal 222 is also presented to a clock input of a flip-flop F/F and is gated into the microprocessor MP through the $T_0$ input. The flip-flop F/F is reset by an output from microprocessor MP through output P26 to ready the system to receive another heartbeat signal.

The microprocessor MP also receives input signals from other sources. A clock input is provided from a 1.92 MHz crystal which controls the operation of the microprocessor MP. A plurality of selectable operating parameter inputs 226 may be provided which affect the various output pulse characteristics. In a clinical situation, these inputs may be set by various external switches. In an implanted situation, these inputs may be provided from another logical command section such as described in U.S. patent application Ser. No. 972,231, filed Dec. 22, 1978. At least one set of outputs 228 is used to set the gain of the variable gain control circuit 206 to insure the proper overall system sensitivity.

The output from the microprocessor MP is pulse signal 230. This output pulse may be for conventional cardiac pacing or may be for tachycardia arrest, such as hereinbelow described. The functional operation of the microprocessor is hereinbelow discussed and appropriate program listings may be made according to the manufacturers instructions. It is obvious that a variety of microprocessors might be used in the system, each of which have their own programming instructions, but which may be programmed in accordance with the flow charts hereinbelow depicted.

Output pulse 230 is presented to the base of transistor T1 which inverts the negative going pulse. The inverted positive signal is now presented to transistor T2, a VMOS N-channel enhancement mode transistor for forming the actual output pulse which is presented to catheter electrode assembly 200. All of the functional relationship shown in FIG. 1 may be performed by the microprocessor MP, and the circuitry interacts as hereinbelow described through catheter electrode assembly 200 with the patient.

The circuitry shown in FIG. 2 may be provided in an external console where the tachycardia arrest system is to be used in a clinical situation. However, the circuitry may also be packaged in the form of an implantable pacer for permanent implantation in an ambulatory patient.

It is apparent that the circuit values shown in FIG. 2 are purely a matter of choice and a variety of components may be used to perform the overall functions therein depicted. A listing of preferred component identification numbers are presented in Table A for purposes of completeness, but a wide variety of acceptable components may be used. The microprocessor depicted herein is available from Intel Corporation as the standard MCS 8748 microcomputer and programmed according to the accompanying instructions. As hereinbelow described, the micro-computer acts to sequence the various system operations until a tachycardia arrest has occurred.

TABLE A

| | |
|---|---|
| T1 | 2N3906 |
| T2 | 2N6660 |
| A1 | TL064 |
| A2 | TL062 |
| A/D | AD7523 |
| C1 | LM339 |
| F/F | MC14013 |
| MP | 8748 |

Figure 4:
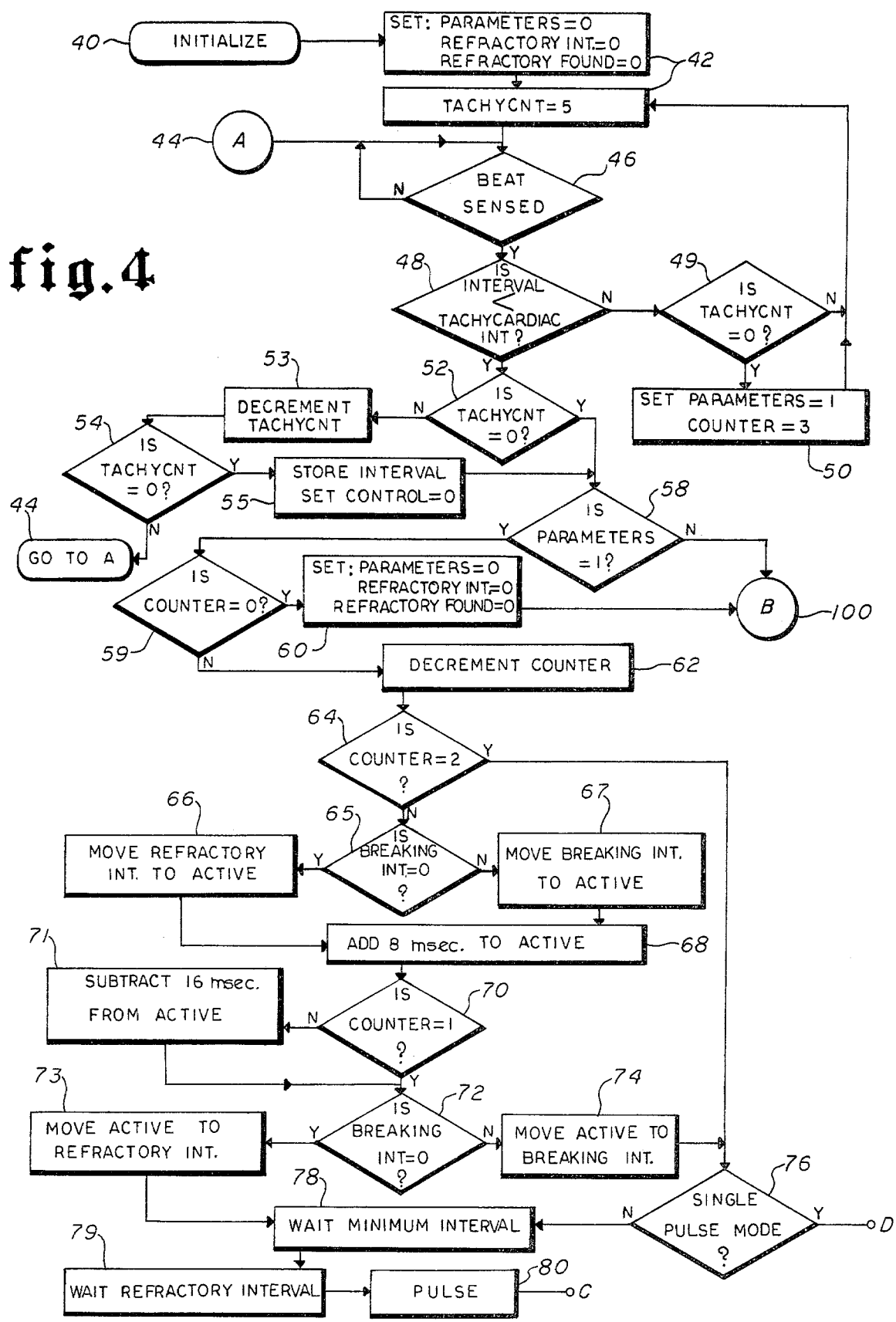
FIG. 4 is a flow control chart for arresting a tachycardia.
Figure 4A:
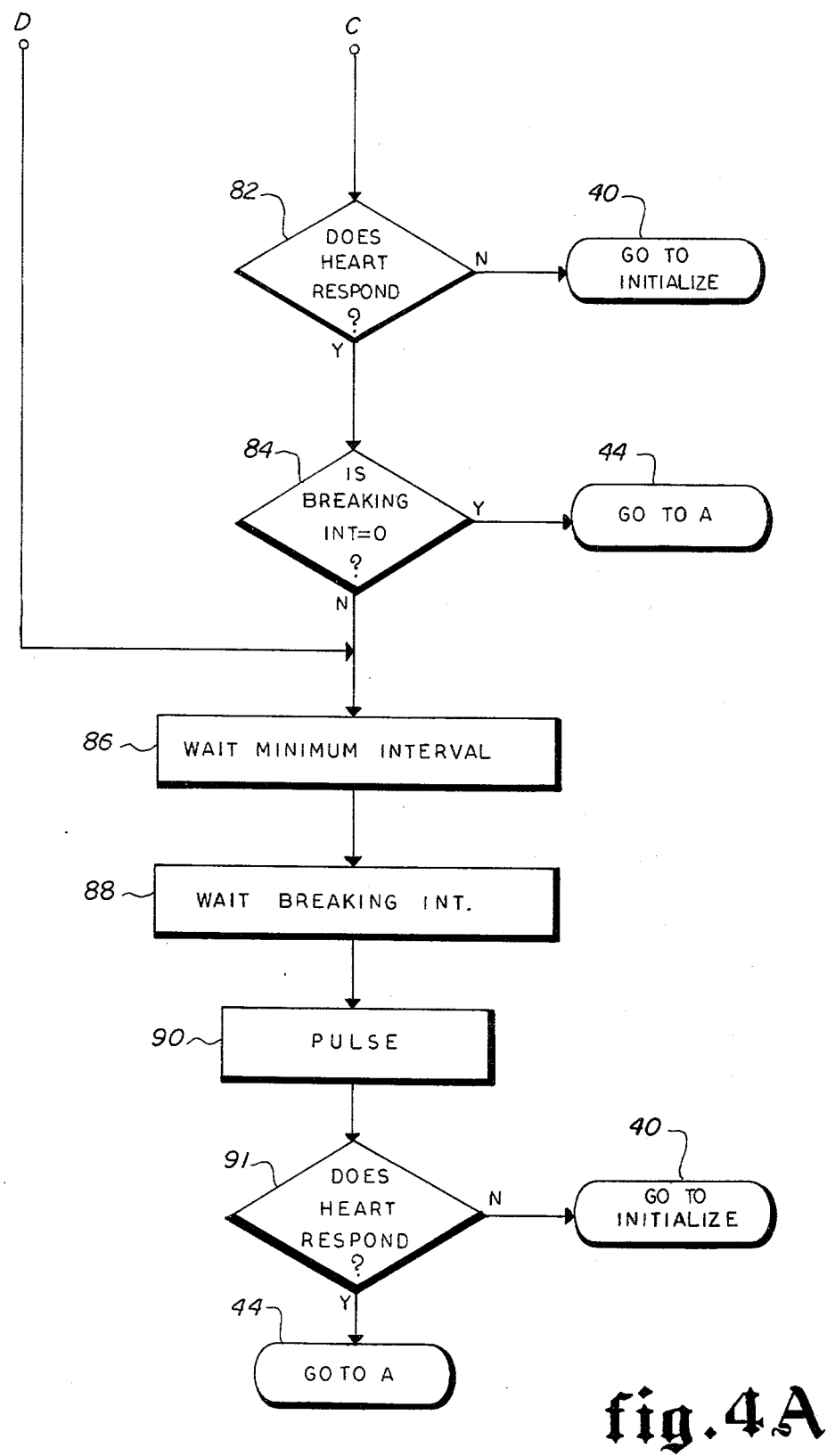
FIG. 4A is a continuation of FIG. 4.
Figure 4B:
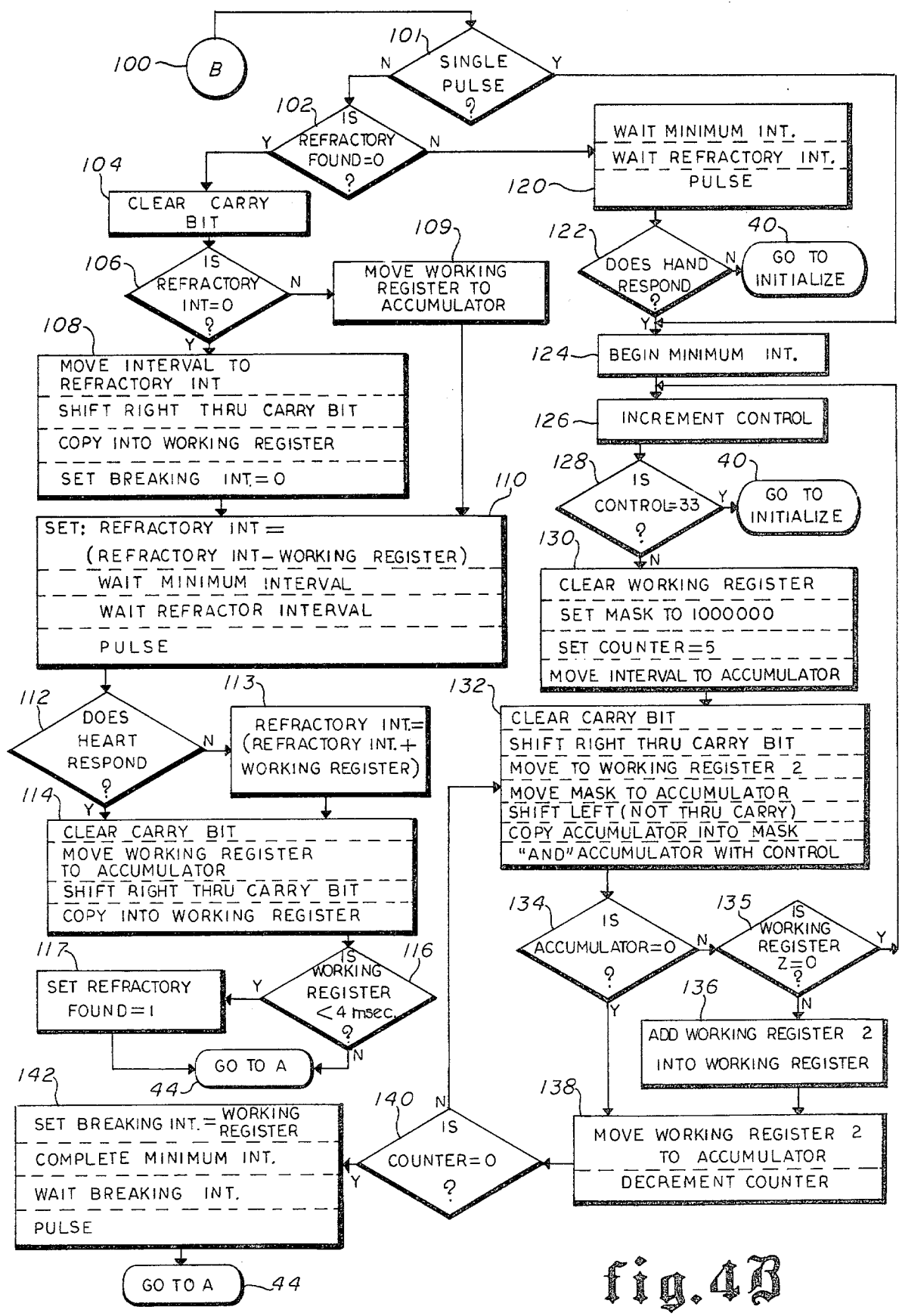
FIG. 4B is a continuation of FIG. 4.

The basic operation of the microprocessor and interaction with the remainder of the pulse generator, sensing electrodes and pacing electrodes may be had by reference to FIGS. 4, 4A and 4B. The diagrams in these figures indicate the basic routine which the microprocessor is programmed to implement and the interface of that routine with outside events. The diagrams are presented in a functional language which is the preferred embodiment of the present invention.

Referring now to FIG. 4, there is first depicted an initial input state 40 which represents the occurrence of a first tachycardia after system installation or the occurrence of failure to arrest a tachycardia when stored parameters are being used, as hereinbelow discussed. In a first condition 42, all conditions are set to initial conditions wherein an entire refractory interval assessment and breaking interval assessment are carried out. The tachycardiac counter is set to the threshold value of 5 and the system is prepared for the occurrence of tachycardia. The sensing electrodes provide an indication of the selected stimulating wave to the beat sensor 12 (see FIG. 1).

If a beat is sensed 46, the interval from the preceeding sensed beat is compared with a selected interval which is determined to represent a tachycardia. If the sensed interval is less than the tachycardia interval 48, the tachycardia pulse count is examined 52 and, if not already at zero, the counter is decremented 53.

If the beat interval is not within the tachycardia range, the tachycardia count is examined 49 to determine whether tachycardia previously existed. If there had been a condition of tachycardia, an arrest has been obtained and the successful parameters are stored. Thus, instruction 50 indicates that successful arrest parameters have been found and also sets the system for applying the successful parameters during a subsequent tachycardia by setting the perturber counter at 3. If there had been a normal condition all along, the system would simply return to original condition 43 by setting the tachycardia count to 5.

Where a tachycardiac interval has been detected and the tachycardia counter decremented, the contents of the tachycardia counter are again examined 54. If the contents are not yet zero, then tachycardia is not yet declared and the system returns to stage 44 for sensing subsequent intervals. Once the contents of the counter reach zero, a condition of tachycardia is declared and the system is set to begin the search for arresting parameters at 55 when the actual tachycardia interval is stored. A control counter for the breaking interval assessor is set at a negative 32 count (binary). It should be noted that the interval stored is an interval between a minimum interval and the measured tachycardia interval. A minimum interval of 200 msec. is conveniently selected to represent an interval within which no recovery from the refractory period would be expected.

Thus, at query 58 the system has either determined that a tachycardia exists or that the system is in the process of arresting the tachycardia. The existence of stored successful parameters is determined at query 58. If successful parameters are not available, then routine B 100 is implemented as hereinbelow explained. If successful parameters are available, the system then looks to the perturber counter 59. A count of zero indicates that all the preselected perturbations have been accomplished without success and the system is reset 60 for a new assessment of successful parameters by routine B 100.

If the pertuber count 59 is greater than zero, the counter is decremented 62 and the contents examined 64. If the perturber count is now 2, the previously successful parameters are applied. The successful parameters may be in either a single pulse mode or the double pulse mode as determined by instruction query 76. In a double pulse mode the output is delayed for the minimum interval 78 and the previously successful refractory interval 79 before an output pulse 80 is delivered by the pulse routine, hereinafter discussed.

The heart response is monitored 82 and if a response is obtained, the system determines whether a successful breaking interval has been stored 84. If a successful breaking interval is stored, the system then waits the minimum interval 86, and the successful breaking interval 88 and delivers a second pulse 90. The response of the heart is then monitored 91. If there is no response, the system resets to initial conditions 40 and an entirely new assessment begins.

If the heart does respond, the system returns to routine A 44 to determine whether the tachycardia has been arrested. If the tachycardia continues, the contents of the perturber counter will no longer be 2 at query 64 and the previously successful parameters may be perturbed in predetermined increments about the successful value to attempt to arrest the tachycardia. A first query 65 determines whether a breaking interval has been stored. If not, the refractory interval is moved to an active register 66 and incremented 68 by 8 msec. If query 65 determines that a breaking interval is available, the breaking interval is moved to an active register 67 and incremented 68 by 8 msec.

The contents of the perturber counter are checked at query 70 to determine whether the selected parameter has been previously perturbed. If not, query 72 again determines whether a breaking interval has been stored and the contents of the active register are moved to the refractory interval storage 73 where there has not been a stored breaking interval or to breaking interval storage 74 where a breaking interval already exists.

If a single pulse mode is selected 76, the pulse is applied only at the breaking interval and the heart response determined. If the coupled pulse mode is established, a first pulse is applied at the end of the refractory period and the second pulse at the end of the breaking interval, as hereinabove discussed.

If the first perturbed parameters are not successful, the perturber counter is again decremented 62 and the system returns to the perturber counter query 70. The perturber counter query 70 now determines that a zero count exists and a second perturbation is accomplished by subtracting 16 msec 71 from the active register 66 or 67 contents. This results in a total of a minus 8 msec. from the original pulse interval for the second perturbation. A single breaking interval pulse or a coupled pulse is then applied as hereinabove described and the heart response again monitored.

If a tachycardia still exists, the contents of the perturber counter will be zero when queried 59 and the system moves to assess new parameters through routine B 100.

Referring now to FIG. 4B, there is shown the system routine for assessing the refractory interval and the breaking interval. The assessment routine first queries 101 whether a single pulse is to be applied or whether a coupled pulse is desired. In a single pulse mode, the routine goes to assess a breaking interval as hereinafter discussed. In a coupled pulse mode, the routine then determines whether a refractory interval is established 102. Where a refractory interval already exists, the routine then goes to assess a breaking interval as hereinafter discussed.

If a refractory interval has not yet been found, the routine then moves to search for the refractory interval. For purposes hereinafter discussed, any carry bit is first cleared 104 from the accumulator and query 106 is made whether any refractory interval is in the working register. If no refractory interval has been tried in the current assessment, the actual tachycardia interval stored at 55 is moved to the refractory interval storage at 108. The first stored interval is known to be outside the refractory period and is therefore divided in half at 108 by simply shifting the stored data and the result is copied into the working register also at 108. Further at 108, the breaking interval is set to zero during the refractory interval assessment. A refractory interval determination 110 is then made by subtracting the contents of the working register from the stored refractory interval and initiating an output pulse routine, hereinafter discussed, at an interval following the last sensed beat determined by the minimum interval plus the refractory interval.

The heart response is then ascertained 112. A condition of no response indicates that the heart was still in the refractory period when the pulse was applied, so a new refractory interval is determined 113 by adding the contents of the working register back to the refractory interval storage. Thus, the refractory interval storage now contains an interval known to be outside the refractory period. A next iteration is begun 114 by again dividing the contents of the working register in half and returning the divided interval to the working register. The contents of the working register are queried 116 and if less than a predetermined interval, the system signals at 117 that the refractory interval is established. If the interval is not sufficiently close to the refractory period, the system will return to a subsequent iteration at 106, as hereinbelow discussed.

The heart response to the output from the refractory interval assessor is detected as hereinabove discussed for FIG. 4 to determine if the tachycardia persists. If the tachycardia is terminated, the parameters are stored at 50 (FIG. 4). If the tachycardia persists, the routine determines at 106 that a first refractory assessment is made and an interval exists in the working register. The contents of the working register 109 were previously determined at 114. A new refractory interval is set 110 by subtracting the contents of the working register from the stored refractory interval and an output pulse applied. The heart response is monitored 112. Again, if there is no response, the refractory interval is increased by adding the working register contents to the previous refractory interval.

It is apparent from FIG. 4B and the above illustration that the refractory interval assessor begins each assessment with an interval known to occur outside the refractory period of the heart. Progressively smaller changes are made until the correction being made is less than four milliseconds. It is arbitrarily determined that this is sufficiently close to the refractory period to indicate the end of the refractory period. It is apparent that other values could be chosen, if desired. Once the correcting interval is determined at 116 to be less than the selected 4 msec interval, the routine determines 117 that the refractory interval has been found.

Thus, when the routine returns to query 102 the condition of the refractory assessment, the routine now moves to the breaking interval assessment. A first pulse is applied 120 at the end of the refractory period and a check 122 is made for heart response. If a response is not indicated, all parameters are set to initial conditions 40 and the entire routine begun anew. If the heart does respond to the refractory interval pulse, the routine begins to wait the minimum interval 124 while determining a first breaking interval. The control counter set at 55 (FIG. 4) is first incremented at 126 and the breaking interval assessor begins to search for a successful breaking interval. The basic interval selected is again the interval between the minimum interval and the tachycardia interval which was stored at 55 (see FIG. 4).

The operation at stages 130, 132, 134, 135, 136, and 138 can best be explained by reference to tables A and B. The initial search is set at 130 by setting the mask and counter. The operation at stages 132, 134, 135, 136, 138, and 140 act to provide the breaking interval equal to a calculated portion of the stored interval at each count of the control cycle. For each of the 32 counts presented by control 126, five counts of the breaking interval assessor are used. Each control count is presented in a binary form and cooperates with the mask to obtain a different breaking assessment interval for each count. Thus, at stage 132, the interval in the accumulator is divided in half and moved to working register 2. The mask is moved to the accumulator and shifted left to present a "1" in the right hand position. The contents of the accumulator are copied back into mask for subsequent use and also compared in a logical "AND" with the binary representation of the control count.

TABLE B

| Count | Mask (Accumulator) | Working Register 2 |
|---|---|---|
| 1 | 0000001 | Int./2 |
| 2 | 0000010 | Int./4 |
| 3 | 0000100 | Int./8 |
| 4 | 0001000 | Int./16 |
| 5 | 0010000 | Int./32 |

TABLE C

| Control | | Working Register | Control | | Working Register |
|---|---|---|---|---|---|
| (1) | 000001 | 1/2 | (17) | 010001 | 17/32 |
| (2) | 000010 | 1/4 | (18) | 010010 | 9/32 |
| (3) | 000011 | 3/4 | (19) | 010011 | 25/32 |
| (4) | 000100 | 1/8 | (20) | 010100 | 5/32 |
| (5) | 000101 | 5/8 | (21) | 010101 | 21/32 |
| (6) | 000110 | 3/8 | (22) | 010110 | 13/32 |
| (7) | 000111 | 7/8 | (23) | 010111 | 29/32 |
| (8) | 001000 | 1/16 | (24) | 011000 | 3/32 |
| (9) | 001001 | 9/16 | (25) | 011001 | 19/32 |
| (10) | 001010 | 5/16 | (26) | 011010 | 11/32 |
| (11) | 001011 | 13/16 | (27) | 011011 | 27/32 |
| (12) | 001100 | 3/16 | (28) | 011100 | 7/32 |
| (13) | 001101 | 11/16 | (29) | 011101 | 23/32 |
| (14) | 001110 | 7/16 | (30) | 011110 | 15/32 |
| (15) | 001111 | 15/16 | (31) | 011111 | 31/32 |
| (16) | 010000 | 1/32 | (32) | 100000 | 0 |

As shown in Table B, for each of the five counts, the mask "1" moves progressively through each of the first five bit locations. In addition, at each of the counts a progressively smaller interval increment is returned to working register 2.

As shown in Table C, the contents of working register 2 are added into the working register whenever there is an output from the logical "AND" at 132. Thus, the contents of the working register present a different portion of the stored interval as the breaking interval at each of the 32 control counts.

After the breaking interval assessor 5 count has been completed at 140, the breaking interval hereinabove determined is set from the contents of the working register, the minimum interval delay is completed and an output pulse routine is initiated after the additional breaking interval.

The response of the heart to the breaking interval pulse is monitored to determine the continuation of the tachycardia. As the control is incremented at 126, a different breaking interval is determined as hereinabove discussed and a pulse is applied at that interval. In the embodiment discussed herein, the basic interval is divided into 1/32 periods and a pulse is eventually applied at 32 distinct points in the interval. If the breaking interval assessment is successful, the parameters are stored at 50 and the system awaits the occurrence of a subsequent tachycardia. It is believed that this spacing is sufficient to provide an output pulse at an interval to arrest most tachycardias.

Figure 3:
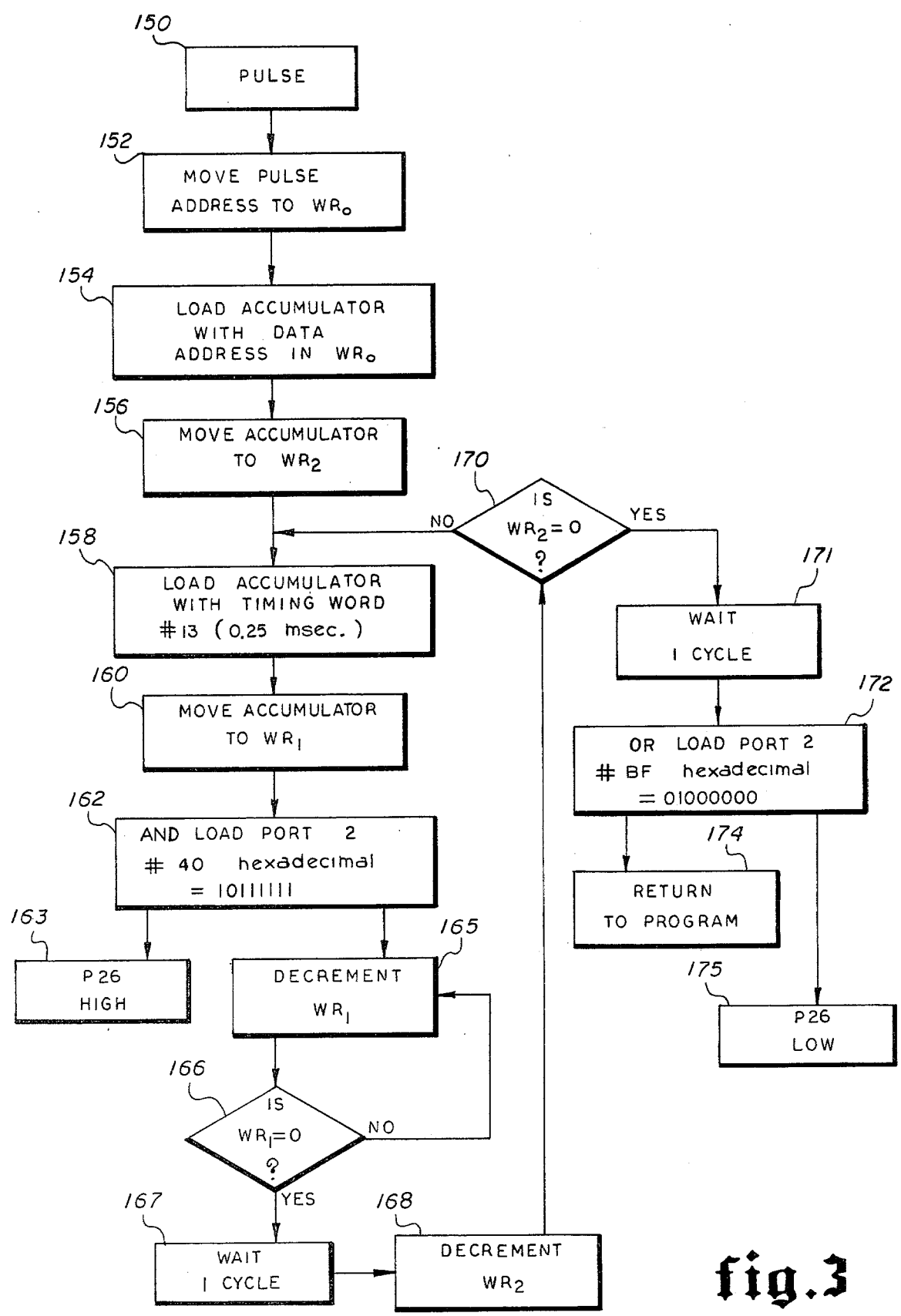
FIG. 3 is a flow control chart for generating an output pulse.

As hereinabove explained, a pulse routine is generated at selected program steps to ascertain the response of the heart to the application of applied stimulus. A preferred embodiment of a pulse routine 150 is depicted in FIG. 3. Pulse routine 150 generates an output for a preselected time period, forming the desired heart stimulus.

When pulse routine 150 is selected, the desired output pulse width is first ascertained. A memory address 152 having a stored count corresponding to the selected number of basic intervals required to form the preselected total pulse width is transferred to working register 0 (WR0) 154, loaded in the accumulator 154, and then transferred to WR2 156.

Next, the accumulator is loaded with the count corresponding to a basic pulse interval 158. In a preferred embodiment, a basic interval of 0.25 msec is provided. At the expected clock frequency of 1.92 MHz, 32 clock pulses will occur during the basic interval. As hereinafter explained, a decimal count of 13 will produce a counting loop yielding the 0.25 msec output.

The selected count is first loaded in WR1 160. To initiate an output pulse on the selected output lead (FIG. 2), binary number 10111111 is AND loaded in the selected output port (Port 2) at 162. Thus an output low level is obtained 163 to initiate the stimulating pulse at the electrode 200 (FIG. 2).

The contents of WR1 are decremented 165 and the total remaining is queried 166. If a remaining total is found, the contents of WR1 are again decremented 165 and queried 165 until a zero count is found. A pause 167 is included to form the total 32 cycles or 0.25 msec for a first basic interval.

When a basic cycle is completed, the contents of $WR_2$ are decremented 168 and queried at 170 to determine whether the selected number of basic intervals is complete. If query 170 indicates that the content of WR2 is not yet zero, the basic interval count is again loaded into the accumulator 158 and the basic cycle repeated. It should be noted that the electrode 200 (FIG. 2) output remains at a low level during this time.

If query 170 indicates that the content of WR2 is zero and the desired width pulse has been applied, the pulse is terminated. First, a pause 171 occurs, followed by OR loading a binary 01000000 into the selected output port (Port 2) at 172. The loading at 172 causes the selected output lead to go high 175, terminating the pulse. The pulse routine 150 then returns 174 to the main routine.

It is readily apparent that the method and apparatus of the present invention operate to apply pulses at predetermined intervals within the period which is effective to arrest a tachycardia. The heart response itself is used to trigger a corresponding arrest attempt. A premeditated search is then carried out for a first pulse to arrest the tachycardia adjacent the end of the refractory interval and, if unsuccessful, a coupled pulse is applied in the interval between the refractory interval and the tachycardia in a prearranged search sequence until the tachycardia is arrested. The heart response is monitored after each arresting try and a subsequent pulse is applied only if the tachycardia persists. Only the minimum stimulation needed to break the tachycardia is applied. This is important to prevent inducing any additional arrhythmias while attempting to arrest the tachycardia.

It is therefore apparent that the present invention is one well adapted to attain all of the objects and advantages hereinabove set forth, together with other advantages which will become obvious and inherent from a description of the apparatus itself. It will be understood that certain combinations and sub-combinations are of utility and may be employed without reference to other features and subcombinations. This is contemplated by and is within the scope of the present invention. It is to be further understood that all matters hereinabove set forth and shown in the accompanying drawings are to be interpreted as illustrative and not in any limiting sense.

What is claimed is:

1. A method for controlling tachycardia, comprising the steps of:
   detecting a tachycardia;
   iniitiating a tachycardia arrest routine when said tachycardia is detected; wherein said routine includes
   generating a first stimulating pulse initiated by a first tachycardia beat within a first trial interval;
   monitoring a cardiac response to said first stimulating pulse;
   increasing or decreasing said first trial interval as a function of said cardiac response to form a second trial interval;
   generating a second stimulating pulse within said second trial interval following a second tachycardiac beat; and
   continuing to derive successive trial intervals and to generate a simulating pulse within each of said trial intervals until said tachycardia is arrested.

2. The method of claim 1, wherein deriving said trial intervals for said stimulating pulses includes the steps of:
   detecting whether the heart is within or without a refractory period when a stimulating pulse is generated; and
   increasing or decreasing said trial interval if said heart is within or without said refractory period, respectively, until the end of said refractory period is determined to a preselected accuracy.

3. The method of claim 2, wherein increasing or decreasing said trial interval comprises the steps of:
   generating one of said stimulating pulses at said derived trial interval after a naturally occurring tachycardiac beat;
   increasing said trial interval if a cardiac beat is not produced by said stimulating pulse or decreasing said trial interval if a cardiac beat is produced by said stimulating pulse; and
   determining a refractory trial interval by generating said stimulating pulses until one of said pulses is generated within a preselected minimum interval after said refractory period or is effective to suppress said tachycardia, whichever event is first detected.

4. The method of claim 3, further including storing said refractory trial interval for said first detected event.

5. The method of claim 4, further including generating said first stimulating pulses at said stored refractory trial interval upon detecting a next tachycardia.

6. The method of claim 1, wherein deriving said trial intervals for said stimulating pulses includes the steps of:
   generating a first series of breaking pulses each applied at first interval increments within said trial interval;
   generating a second series of breaking pulses, each applied at second interval increments smaller than said first interval increments;
   generating successive series of breaking pulses at progressively smaller interval increments until a tachycardia breaking interval is determined of said interval increments reach a predetermined minimum value;
   each one of said breaking pulses being generated after each tachycardiac beat at a unique interval within said trial interval.

7. The method of claim 6, wherein determining said breaking interval includes the steps of:
   determining a search interval initiated at a preselected minimum interval after a tachycardiac beat and terminated at the following tachycardiac beat,
   generating a plurality of breaking assessment pulses in a preselected pattern within said search interval, and
   terminating said breaking assessment pulses when said tachycardia is suppressed.

8. The method of claim 6, further including storing said tachycardia breaking interval.

9. The method of claim 8, further including generating a first stimulating pulse at said stored tachycardia breaking interval upon detecting a next tachycardia.

10. A method for controlling tachycardia, comprising the steps of:
   detecting time intervals between successive beats of a heart;

monitoring said time intervals to detect a tachycardia;

initiating a tachycardia arrest routine when said tachycardia is detected, wherein said routine includes:

generating a refractory period pulse at a first stored trial interval after a tachycardiac beat approximating a refractory period for said heart; and thereafter generating a breaking pulse at a second stored trial interval after said tachycardiac beat and determined effective to arrest a previous tachycardia.

11. The method of claim 10, further including the step of monitoring cardiac response to each of said refractory period and said breaking pulses.

12. The method of claim 11, including the step of initiating a perturbation routine for at least one of said stored trial intervals where tachycardia is detected after generating said refractory period pulse and said breaking pulse.

13. The method of claim 12, including the steps of:

monitoring cardiac response after each of said perturbations, initiating a succeeding perturbation when tachycardia is detected, and terminating said perturbation routine when tachycardia is arrested.

14. The method of claim 13, including the steps of detecting the continued occurrence of tachycardia after a predetermined number of said perturbations, and thereafter initiating a search routine for new time intervals for said refractory period pulse and said breaking pulse.

15. The method of claim 11, including the step of:

returning said tachycardia arrest routine to an initial condition where no cardiac response is detected following said refractory period pulse or said breaking pulse.

16. The method of claim 11, including the step of:

initiating a search routine for new trial intervals for said refractory period pulse and said breaking pulse when a preselected cardiac response is not produced by said pulses generated at said first or second stored trial intervals.

17. The method of claim 16, including the steps of:

determining whether said heart is within or without said refractory period when said refractory period pulse is applied;

increasing or decreasing said trial interval if said heart is within or without said refractory period, respectively, until the end of said refractory period is determined to a preselected accuracy;

generating a refractory period pulse at the end of said refractory period, monitoring said heart response to said refractory period pulse, and thereafter deriving a trial interval for generating a breaking interval pulse effective to arrest said tachycardia where said refractory period pulse is ineffective to arrest said tachycardia.

18. The method of claim 17, wherein determining said refractory period comprises the steps of:

generating said first stimulating pulse at a predetermined time after a naturally occurring tachycardiac beat, monitoring cardiac response to said first stimulating pulse, generating a plurality of stimulating pulses in an iterative sequence of variable time intervals functionally determined by the occurrence of cardiac response, and terminating said plurality of pulses upon generating a stimulating pulse within a preselected minimum interval after said refractory period or upon suppressing said tachycardia, whichever event is first detected.

19. The method of claim 18, further including storing said refractory trial interval for said first detected event.

20. The method of claim 19, further including generating said first stimulating pulse at said stored refractory period upon detecting a next tachycardia.

21. The method of claims 17, 18, 19 or 20, wherein deriving said trial interval for said breaking interval pulse includes the following steps:

generating a first series of breaking pulses each applied at first interval increments within said trial interval;

generating a second series of breaking pulses, each applied at second interval increments smaller than said first interval increments; and generating successive series of breaking pulses at progressively smaller interval increments until a tachycardia breaking interval is determined or said interval increments reach a predetermined minimum value;

each one of said breaking pulses being generated after each tachycardiac beat at a unique interval within said trial interval.

22. The method of claim 21, further including storing said breaking interval effective to suppress said tachycardia.

23. Apparatus for controlling tachycardia, comprising:

means adapted to determine time intervals between successive cardiac beats for detecting a tachycardiac condition;

means for initiating a tachycardia arrest routine when said tachycardia is detected, including means for generating a first stimulating pulse initiated by a first tachycardiac beat within a first trial interval; and means for generating a signal indicative of a cardiac response to said first stimulating pulse;

means for increasing or decreasing said first trial interval as a function of said cardiac response signal to form a second trial interval;

means for generating a second stimulating pulse within said second trial interval following a second tachycardiac beat; and means for continuing to derive successive trial intervals and to generate a stimulating pulse within each of said trial intervals until said tachycardia is arrested.

24. The apparatus of claim 23, wherein said means for deriving said successive trial intervals includes:

means for deriving a signal indicative of whether the heart is within or without a refractory period when a stimulating pulse is generated;

means for increasing or decreasing said trial interval responsive to said refractory period signal until the end of said refractory period is determined to a preselected accuracy.

25. The apparatus of claim 24, wherein said means for increasing or decreasing said trial interval comprises:

means for generating one of said stimulating pulses at said derived trial interval after a naturally occurring tachycardiac beat;

means for increasing said trial interval if a cardiac beat is not detected following said stimulating pulse and for decreasing said trial interval if a cardiac beat is produced by said stimulating pulse; and means for determining a refractory trial interval by generating said stimulating pulses until one of said pulses is generated within a preselected minimum interval after said refractory period or is effective to suppress said tachycardia, whichever event is first detected.

26. The apparatus of claim 25, further including means for storing said refractory trial interval for said first detected event.

27. The apparatus of claim 26, further including means for generating said first stimulating pulse at said stored refractory trial interval upon detecting a next tachycardia.

28. The apparatus of claim 23 or claim 24, wherein said means for deriving said trial intervals includes:

means for generating a first series of breaking pulses, each applied at first interval increments within said trial interval;

means for generating a second series of breaking pulses, each applied at second interval increments smaller than said first interval increments;

means for generating successive series of breaking pulses at progressively smaller interval increments until a tachycardia breaking interval is determined or said interval increments reach a predetermined minimum value;

each one of said stimulating pulses being generated after each tachycardiac beat at a unique interval within said trial interval.

29. The apparatus of claim 28, wherein said means for determining said breaking interval includes the steps of:

means for determining a search interval initiated at a preselected minimum interval after a tachycardiac beat and terminated at the following tachycardiac beat, means for generating a plurality of breaking assessment pulses in a preselected pattern within said search interval, and means for terminating said breaking assessment pulses when said tachycardia is suppressed.

30. The apparatus of claim 29, further including means for storing said tachycardia breaking interval.

31. The apparatus of claim 30, further including means for generating a first stimulating pulse at said stored tachycardia breaking interval upon detecting a next tachycardia.

32. A method for controlling tachycardia, comprising the steps of:

generating a heart stimulating pulse at a succession of trial intervals from naturally occurring heart beats to derive a refractory trial interval ending within a preselected time after the refractory period of the heart;

generating a refractory period pulse at said refractory trial interval; and thereafter generating a second breaking pulse at a breaking interval effective to terminate said tachycardia.

33. A method according to claim 32, wherein said breaking interval is derived by appling said breaking pulse in a succession of breaking trial intervals following said refractory period pulses until said breaking interval effective to terminate said tachycardia is derived.

34. Apparatus for controlling tachycardia, comprising:

means for generating input electrical signals indicative of the occurrence of a heart beat;

means for generating output electrical signals suitable for stimulating a heart; and a microprocessor for correlating said input signals with said output signals for deriving a timed relationship therebetween effective to terminate a tachycardia.

35. Apparatus according to claim 34, further including means for storing said timed relationship for use as an initial relationship in subsequent correlating of said input signal with said output signal.

* * * * *